(12) United States Patent
Lindemann et al.

(10) Patent No.: US 6,402,747 B1
(45) Date of Patent: Jun. 11, 2002

(54) HANDSWITCH CORD AND CIRCUIT

(75) Inventors: Russell Wayne Lindemann, Longmont; David Nichols Heard, Boulder, both of CO (US)

(73) Assignee: Sherwood Services AG, Schaffhausen (CH)

(*) Notice: Subject to any disclaimer, the term of this patent is extended or adjusted under 35 U.S.C. 154(b) by 0 days.

(21) Appl. No.: 09/783,048

(22) Filed: Feb. 13, 2001

Related U.S. Application Data

(63) Continuation of application No. 08/897,404, filed on Jul. 21, 1997, now abandoned.

(51) Int. Cl.[7] ............................................. A61B 18/18
(52) U.S. Cl. ........................... 606/42; 606/45; 606/37
(58) Field of Search ..................... 606/32–34, 37–42, 606/45, 48–52

(56) References Cited

U.S. PATENT DOCUMENTS

| | | | |
|---|---|---|---|
| 2,827,056 A | 3/1958 | Degelman | |
| 3,494,363 A | 2/1970 | Jackson | |
| 3,752,160 A | 8/1973 | Billin | |
| 4,370,980 A | * 2/1983 | Lottick | 606/42 |
| 4,463,759 A | * 8/1984 | Garito et al. | 606/42 |
| 4,552,143 A | 11/1985 | Lottick | |
| 5,196,007 A | * 3/1993 | Ellman et al. | 606/32 |
| 5,246,440 A | * 9/1993 | Van Noord | 606/39 |
| 5,472,442 A | * 12/1995 | Klicek | 606/42 |

* cited by examiner

Primary Examiner—Michael Peffley

(57) ABSTRACT

A replaceable accessory cord and handswitch set adapted for use with an electrosurgical instrument that has a proximal end handle for holding by the surgeon and distal end effectors for delivery of electrosurgery to a patient. A replaceable accessory cord is adapted to electrically couple an electrosurgical generator to the instrument with two or more conductors. A handswitch with normally open contacts is near the proximal end. One of the contacts attaches to an active conductor and another of the conductors connected to the other contact. A receptacle on the handswitch connects electrically to the contact. An insulated support on the handswitch engages the instrument preventing relative movement. A button on the support is accessible to the surgeon, but remote from the receptacle land the terminal. The button is electrically isolated from the contacts, the receptacle, the terminal and the conductors. The button moves on the support for closing the contacts and is positioned for control by the surgeon's finger. The handswitch controls delivery of a coagulating wave form and a cutting wave form.

12 Claims, 4 Drawing Sheets

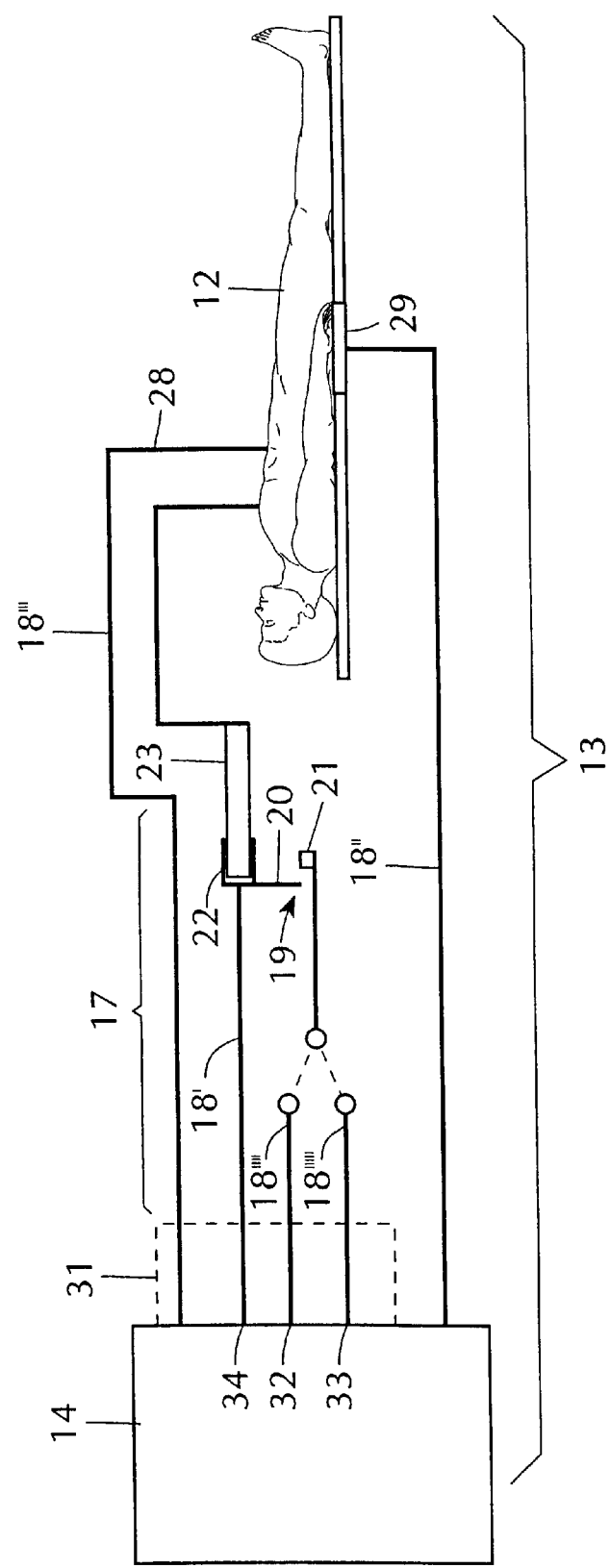

HANDSWITCH CORD AND CIRCUIT

This application is a continuation of application Ser. No. 08/897,404 filed Jul. 21, 1997, now abandoned.

FIELD OF THE INVENTION

This invention relates to a special replaceable accessory cord and handswitch set for use with an electrosurgical instrument having no handswitch. More particularly, a replaceable accessory cord and handswitch are supported on a terminal of the electrosurgical instrument so the handswitch is accessible to the surgeon controlling the electrosurgical energy delivery to a patient.

BACKGROUND OF THE INVENTION

Any electrosurgical instrument, such as scissors, graspers, forceps and the like receive electrosurgical energy from an electrosurgical generator. A foot switch or hand switch controls the application of electrosurgical energy to the electrosurgical instrument. Surgeons frequently prefer the convenience of using a hand switch. Since one hand of the surgeon holds the electrosurgical instrument, the finger actuation of a switch on the electrosurgical instrument is convenient.

To minimize the cost of such electrosurgical instruments, suppliers frequently provide them without an integral handswitch for use by the surgeon. That omission benefits cleanability and sterilization after use, if it is a reusable electrosurgical instrument and minimizes replacement cost if it is disposable. Consideration of the addition of a convenient finger switch may not be worth added expense.

Control of high frequency electrosurgical energy at the electrosurgical instrument has long been a problem addressed in many ways. The use of fluidic control disclosed in U.S. Pat. No. 3,494,363 teaches squeezing a bulb or closing a vacuum port by the surgeon to control electrosurgical energy delivery to a forceps. U.S. Pat. No. 3,752,160 is a disposable electrode switch attached to a forceps and functional when the tines are squeezed together. In particular, the electrosurgical energy is transmitted in a monopolar application when a terminal on the cord contacts bare metal on the forceps. U.S. Pat. Nos. 4,370,980 and 4,552,143 have removable handswitches for electrocautery instruments. Conductive spring clips attach the handswitches to an electrosurgical instrument such as, scissors or a forceps. The electrically wired handswitch allows energy passage through electrically conductive clips for attachment to the electrosurgical instrument. Cutting or cauterizing electrosurgical energy passing through the handswitch depends on the operation of the button by the surgeon. Insulated handles of the electrosurgical instrument protect the surgeon from the electrosurgical energy but nothing protects the surgeon from the exposed conductive spring clips.

There has been a need to convert existing standard electrosurgical instruments such as, Endopath instruments by Johnson & Johnson or the Endo products of United States Surgical Corporation to hand switching with a simple and low cost replaceable accessory cord and handswitch set. No combination of a replaceable accessory cord and hand switch set attaches to where the regular cord set connects to afford finger switching. No combination replaceable accessory cord and handswitch set insulates the electrical connection of the connection. No replaceable cord and handswitch set provides a mechanical connection to support remotely disposed switch button. No replaceable cord and handswitch set provides secure attachment resistant to longitudinal movement and lateral movement relative to the electrosurgical instrument. No replaceable cord and handswitch set provides secure insulated electrical connection and an attachment for finger actuation of the switch button positioned to resist to longitudinal and lateral movement.

SUMMARY OF THE INVENTION

A replaceable accessory cord and handswitch set for use with an electrosurgical instrument by a surgeon on a patient in an electrosurgical circuit preferably connects between an electrosurgical generator, the electrosurgical instrument. The electrosurgical instrument for electrical connection to the electrosurgical generator in the circuit may have a proximal end for holding by the surgeon and a distal end for delivery therefrom of electrosurgery to the patient. A cord for electrically coupling to the electrosurgical generator most preferably supplies electrosurgery to the electrosurgical instrument with two or more conductors.

A handswitch electrically and removeably couples to one of the conductors and is preferably located on the replaceable accessory cord near the proximal end of the electrosurgical instrument for access by the surgeon. The handswitch is in the electrosurgical circuit. A pair of normally open contacts in the handswitch may preferably have one of the contacts attached to the active conductor and with either a cut waveform or a coagulation waveform conductor connected to the other contact. A receptacle on the handswitch can connect electrically to the active contact in the preferred embodiment. A terminal on the electrosurgical instrument may be configured to conjugate with the receptacle so the terminal would be in electrical contact with the active conductor.

A support on the handswitch for engagement with the electrosurgical instrument prevents movement relative therebetween. The support most preferably is electrically insulated from the pair of contacts, the receptacle, the terminal and the conductors. An operating button on the support may preferably be accessible to the surgeon. The operating button, positioned remotely from the receptacle and the terminal, is most preferably electrically isolated from the pair of contacts, the receptacle, the terminal and the conductors. The operating button mounts for movement relative to the support and for closing the pair of contacts during use of the electrosurgical instrument when applying electrosurgical energy to the patient.

A handle is on the preferred embodiment of the electrosurgical instrument for use by the surgeon. One or more end effectors on the electrosurgical instrument preferably may apply electrosurgical energy. The support and operating button might be physically located on the handle so when the electrosurgical instrument is grasped by the handle the operating button is positioned for control by the surgeon's finger of electrosurgical energy delivery. The handle is preferably insulated and at the proximal end of the electrosurgical instrument and the one or more electrosurgical effectors may be located opposite the handle at the distal end of the electrosurgical instrument. The one or more end effectors could include scissors, graspers. The one or more end effectors may alternately be a bipolar circuit with a return located on one of the end effectors. The return is connected to a return conductor for completing the electrosurgical circuit. The one or more end effectors when in a monopolar circuit can have a return pad on the patient as a part of the electrosurgical circuit.

The terminal most preferably is positioned near the proximal end of the electrosurgical instrument. The electrosurgical circuit for electrosurgical instrument for use by a surgeon on a patient may include one or more end effectors on the electrosurgical instrument for contact with the patient's tissue during application of electrosurgical energy by the surgeon. The handle on the electrosurgical instrument could be at an end thereof opposite the one or more end effectors for positioning the one or more end effectors by the surgeon during the application of electrosurgical energy. The terminal on the electrosurgical instrument near the handle may receive electrosurgical energy for the one or more end effectors and may be electrically insulated from the handle. The handswitch removeably, electrically and mechanically can be connected and supported by the terminal. The handswitch is preferably electrically coupled to the terminal and the electrosurgical energy. The cord may detachably and electrically couple to the handswitch with one or more conductors therein for delivery of electrosurgical energy to the one or more end effectors. The electrosurgical generator can connect to the active conductor for supply of electrosurgical energy to the electrosurgical instrument handswitch. The electrosurgical generator connects to the return conductors coupled to one of the end effectors for return of the electrosurgical energy to the electrosurgical generator.

A button on the handswitch for closing the handswitch may apply electrosurgical energy to the one or more end effectors so as to be accessible to the handle so that electrosurgical energy can be selectively applied by the surgeon to the one or more end effectors. A support for the button may mount the button for finger actuation by the surgeon. The support can carry the button for movement relative thereto during actuation of the handswitch. The support for mechanically a connecting to the handle most preferably prevents relative movement therebetween.

The support electrically insulates from the button and the handswitch for preferably preventing leakage, stray currents or grounding to the surgeon. The support might include a pressure sensitive adhesive thereon to secure the button on the handle for access by a finger of the surgeon.

The electrosurgical generator and the cord electrically couple to the handswitch for allowing the selective electrically connection through conductors in the cord to effect the delivery of electrosurgical energy to the one or more end effectors. The cord can include a plug for removeably connecting the conductors to the electrosurgical generator. The handswitch may control the electrosurgical generator to cause delivery therefrom of electrosurgical energy with a coagulating wave form to the one or more end effectors. The electrosurgical instrument is preferably elongate between the handle and the one or more end effectors so that laparoscopic electrosurgery may be performed by the surgeon with control by the handswitch. A return may be connected to one of the end effectors for bipolar electrosurgery.

BRIEF DESCRIPTION OF THE DRAWINGS

FIG. 5 is a schematic of a circuit diagram showing the electrosurgical circuit between the electrosurgical generator and the electrosurgical instrument.

DETAILED DESCRIPTION OF THE INVENTION

Figure 1:
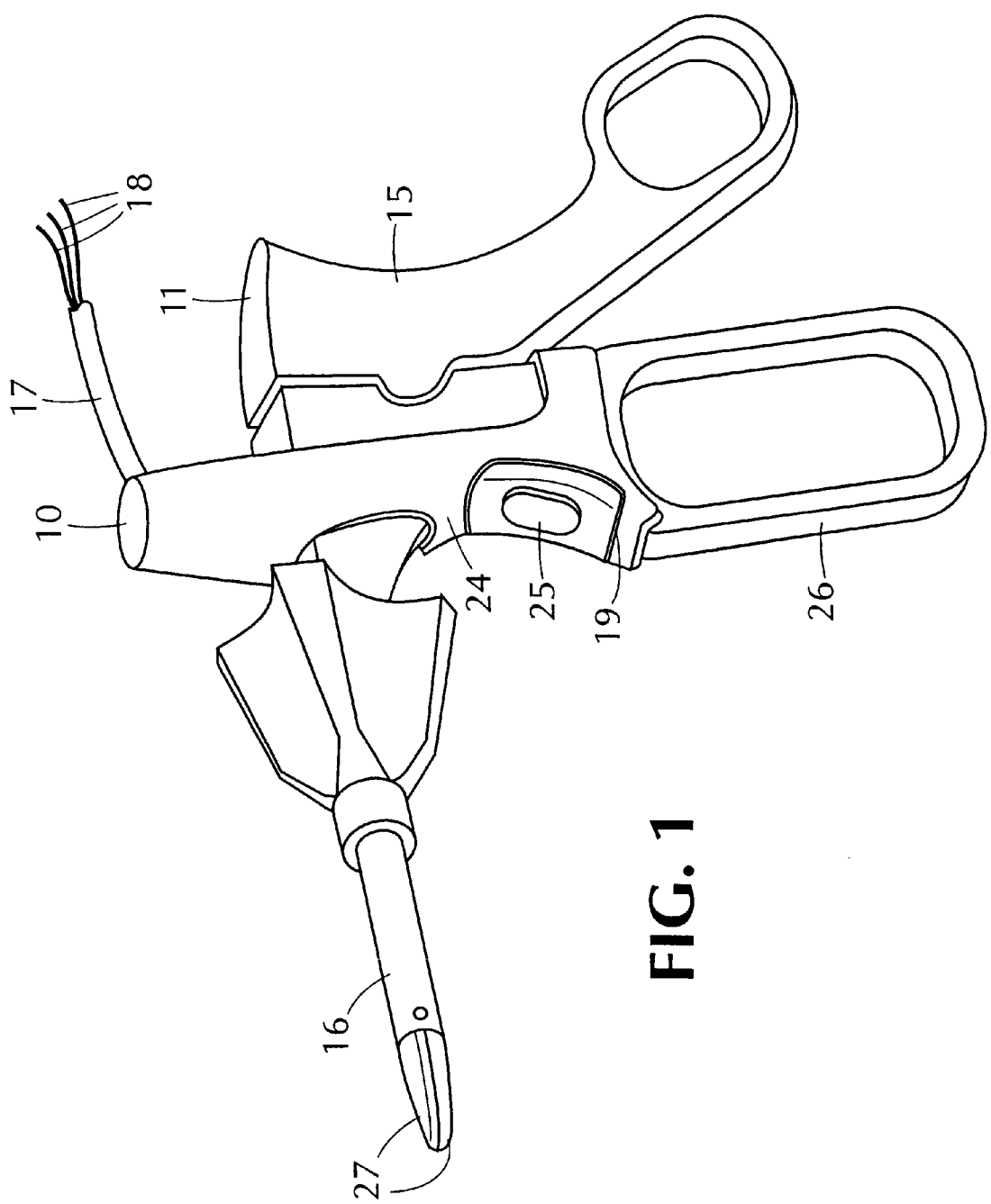
FIG. 1 is a perspective view of the replaceable accessory cord and handswitch set of the preferred embodiment shown on endosurgical instrument such as those made by Ethicon Endo-Surgery of Johnson & Johnson.
Figure 2:
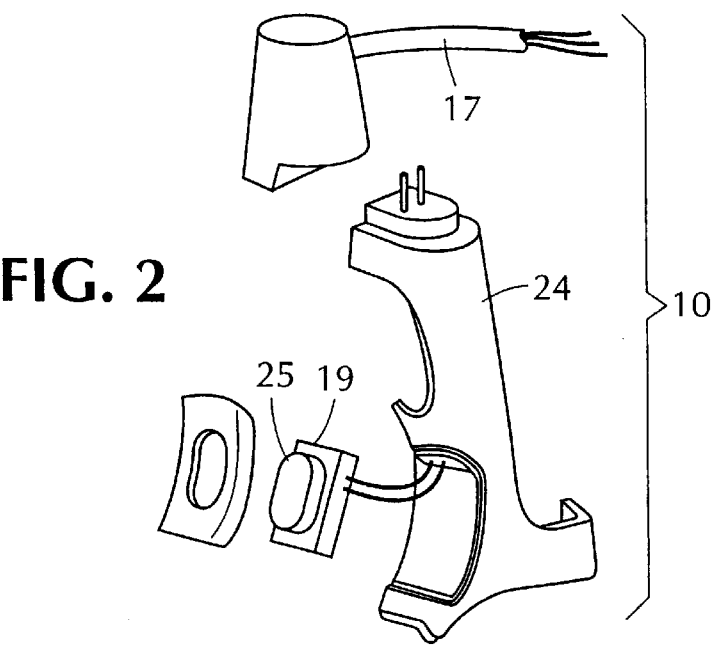
FIG. 2 is a perspective exploded view showing a two piece construction of the replaceable accessory cord and handswitch set of FIG. 1.
Figure 3:
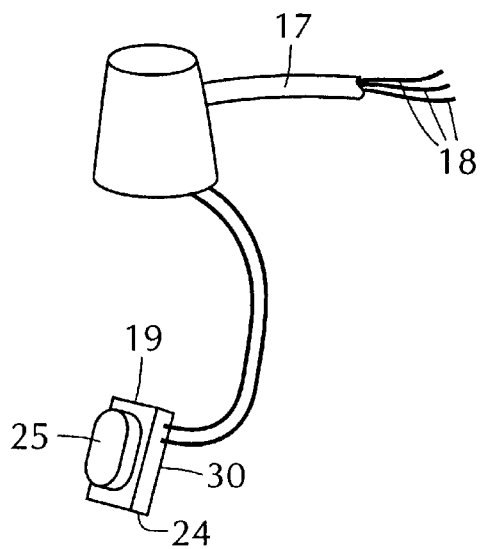
FIG. 3 is a perspective view showing a replaceable accessory cord and handswitch set of another alternate embodiment wherein the switch is separate from the receptacle for pressure sensitive application to the handle of any electrosurgical instrument.

A replaceable accessory cord and handswitch set 10 for use with an electrosurgical instrument 11 by a surgeon on a patient 12 in an electrosurgical circuit 13 is shown in FIGS. 1 through 5. The electrosurgical circuit 13 connects between an electrosurgical generator 14 and the electrosurgical instrument 11. The electrosurgical instrument 11 for electrical connection to the electrosurgical generator 14 in the circuit 13 has a proximal end 15 for holding by the surgeon and a distal end 16 for delivery therefrom of electrosurgery to the patient 12. A cord 17 in FIGS. 1 to 5 for electrically coupling to the electrosurgical generator 14 supplies electrosurgery to the electrosurgical instrument 11. The cord 17 has two or more conductors 18. Best shown schematically in FIG. 5 is the active or power conductor 18', the return conductor (monopolar) 18", the return conductor (bipolar) 18''', the cut signal conductor 18'''' and the coagulation signal conductor 18'''''.

A handswitch 19 selectively and electrically in series with one of the signal conductors 18'''' or 18''''' and is located on the replaceable accessory cord 17 near the proximal end 15 of the electrosurgical instrument 11 for access by the surgeon. The handswitch 19 is in the electrosurgical circuit 13. A pair of normally open contacts 20 and 21 in the handswitch 19 have contact 20 attached to the active conductor 18' and the other of the signal conductors 18'''' or 18''''' connected to the other contact 21. A receptacle 22 connects to the active conductor 18'. A terminal 23 on the electrosurgical instrument 11 is configured to conjugate with the receptacle 22 so the terminal 23 would be in electrical contact with the other conductor 18' as best shown in FIGS. 4 and 5.

A support 24 in FIGS. 1, 2, 3 and 4 on the handswitch 19 for engagement with the electrosurgical instrument 11 prevents movement relative thereto. The support 19 is electrically insulated from the pair of contacts 20 and 21, the receptacle 22, the terminal 23 and the conductors 18. An operating button 25 on the support 24 is accessible to the surgeon. The operating button 25 is electrically isolated from the pair of contacts 20 and 21, the receptacle 22, the terminal 23 and the conductors 18 in FIG. 4. The operating button 25 moves relative to the support 24 for closing the normally open pair of contacts 20 and 21 during use of the electrosurgical instrument 11. When applying electrosurgical energy to the patient 12, the surgeon's finger closes contacts 20 and 21.

Figure 4:
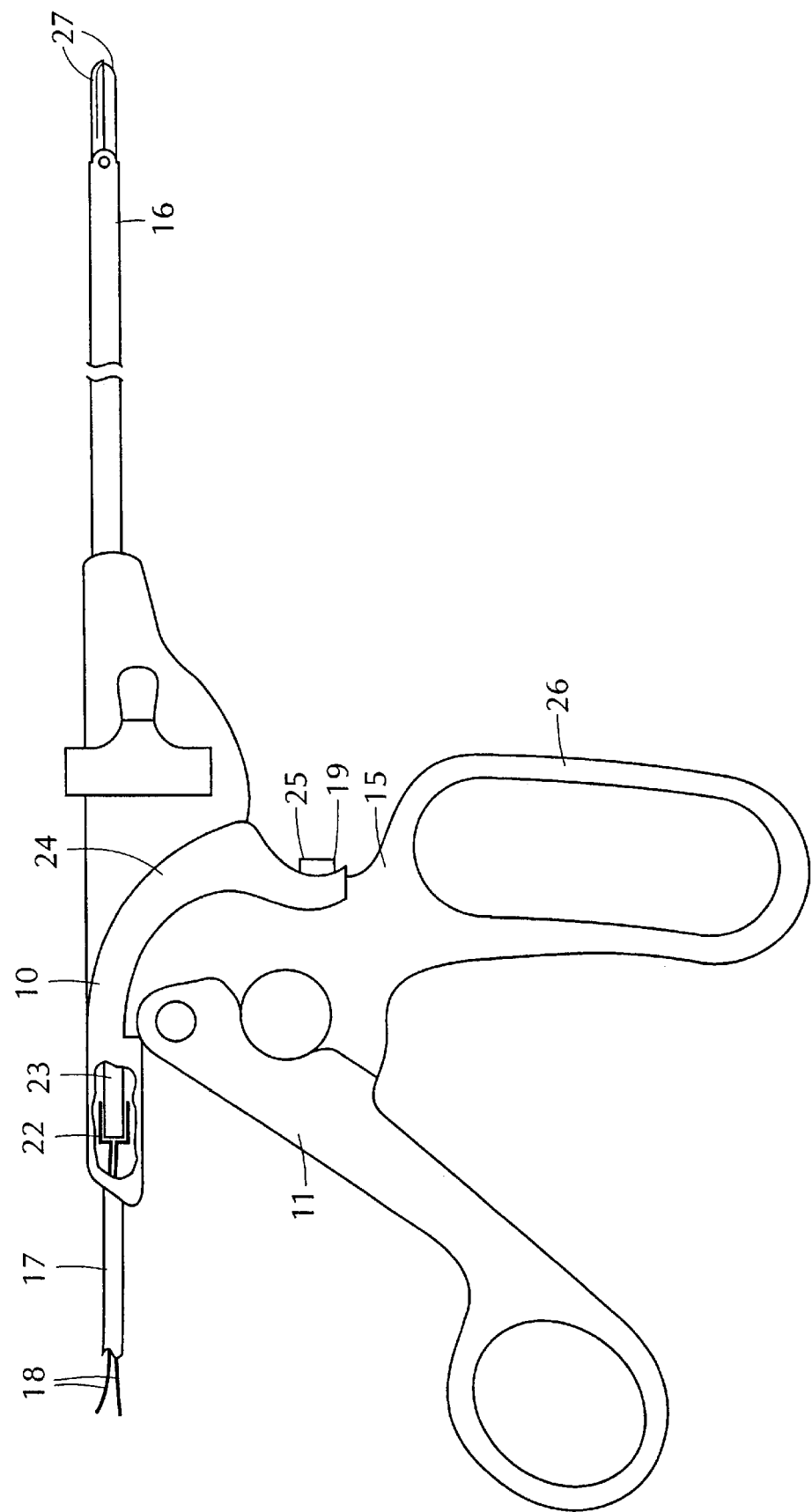
FIG. 4 is a perspective view of the replaceable accessory cord and handswitch set of an alternate embodiment shown on endosurgical instrument such as made by United States Surgical Corporation.

A handle 26 in FIGS. 1 and 4 is on the proximal end 15 of the electrosurgical instrument 11 for use by the surgeon. One or more end effectors 27 on the electrosurgical instrument 11 distal end 16 apply electrosurgical energy. The support 24 and operating button 25 are physically located on the handle 26 so when the electrosurgical instrument 11 is grasped by the handle 26 the operating button 25 is positioned for control by the surgeon's finger of electrosurgical energy delivery. The handle 26 is insulated and at the proximal end 15 for the electrosurgical instrument 11. The one or more electrosurgical effectors 27 are located opposite the handle at the distal end 16 of the electrosurgical instrument 11 as seen in FIGS. 1 and 4. The one or more end effectors 27 could include scissors 28 as in FIG. 4 or could have graspers as in FIG. 1 or hooks (not shown). When one or more end effectors 27 are in a bipolar circuit, there is a return 28 as shown in FIG. 5. The end effector for return is connected to the return conductor 18''' for completing the electrosurgical circuit 13. When one or more end effectors 27 are in a monopolar circuit, there is a return pad 29 on the patient 12 as a part of the electrosurgical circuit 13 through conductor 18'' as in FIG. 5. The terminal 23 is positioned near the proximal end 15 of the electrosurgical instrument 11 as seen in FIGS. 1 and 4.

The electrosurgical circuit 13 for the electrosurgical instrument 11 for use by the surgeon on the patient 12 has one or more end effectors 27 on the electrosurgical instrument 11 for contact with the patient's tissue during application of electrosurgical energy by the surgeon. The handle 26 on the electrosurgical instrument 11 is at the proximal end 15 thereof opposite the one or more end effectors 27 for positioning the one or more end effectors 27 by the surgeon during the application of electrosurgical energy. The terminal 23 on the electrosurgical instrument 11 near the handle 26 receives electrosurgical energy for the one or more end effectors 27 and terminal 23 is electrically insulated from the handle 26. The handswitch 19 removeably, electrically and mechanically is connected and is supported by the terminal 23 as shown in FIGS. 1 to 4. The handswitch 19 electrically couples to the terminal 23 and the the signal conductor 18'''' or 18''''' so that electrosurgical energy can be selectively applied by the surgeon to the one or more end effectors 27. Cord 17 electrically couples to the handswitch 19 with one or more conductors 18 therein for delivery of electrosurgical energy to the one or more end effectors 27. Electrosurgical generator 14 connects to the active conductor 18' for supply of electrosurgical energy to the electrosurgical instrument 11 handswitch 19 as shown schematically in FIG. 5. The electrosurgical generator 14 connects to another of the conductors 18''' coupled to one of the end effectors 27 for return of the electrosurgical energy to the electrosurgical generator 14 when use in a bipolar procedure.

Button 25 on the handswitch 19 for closing the pair of contacts 20 and 21 applies electrosurgical energy to the one or more end effectors 27. Support 24 for the button 25 mounts the button 25 for finger actuation by the surgeon. The support 24 carries the button 25 allowing movement relative to the support 24 during actuation of the handswitch 19. The support 24 mechanically connects to the handle 26 preventing relative movement therebetween. The support 24 in the alternate of FIG. 3 includes a pressure sensitive adhesive 30 thereon to secure the button 25 on handle 26 for access by a finger of the surgeon. While the cord 17 is shown permanently attached to the handswitch 19 in the FIGS. 1 to 4, skilled artisans will know that a connector such as in FIG. 2 could be used to allow the separation of the cord 17 and the handswitch 19.

Electrosurgical generator 14 and cord set 10 electrically couple to the handswitch 19 for allowing the selective electrically connection through conductors 18 in the cord 17 to effect the delivery of electrosurgical energy to the one or more end effectors 27. The cord 17 has a plug 31 shown schematically in FIG. 5 as a dashed line for removeably connecting the conductors 18', 18''', 18'''' and 18''''' to the electrosurgical generator 14. The handswitch 19 controls the electrosurgical generator 14 to preferably cause delivery therefrom of electrosurgical energy with a coagulating wave form to the one or more end effectors 27.

Although not shown in the FIGS. 1 and 4, the electrosurgical instrument 11 is elongate between the handle 26 and the one or more end effectors 27 so that laparoscopic electrosurgery may be performed by the surgeon with control by the handswitch 19.

For bipolar surgery, the electrosurgical generator 14 connects to one of the return conductors 18''' in the cord 17 through plug 31. An active electrosurgical output of the electrosurgical generator 14 supplies the high frequency waveform. Cutting or coagulation waveforms differ in their shapes and tissue effects. Typically the plug 31 and the electrosurgical generator 14 have three conjugating connections, one for a cut signal 32, one for a coagulation signal 33 and one for the active electrosurgical active output 34. Handswitch 19 selection could be arranged for coagulation or cutting, two buttons could provide the choice therebetween or a switch 35 could as shown in FIG. 5 be set to either cutting or coagulation.

Selection of cutting or coagulation waveforms is shown schematically in FIG. 5 with a switch 35 which connects either cut conductor 18'''' or coagulation conductor 18''''' to contact 21. That switch 35 could be on plug 31, in electrosurgical generator 14, in the cord 17 or on the handswitch 19. If on the latter, then the button 25 could be split or a rocker as is common on electrosurgical pencils with integral switching.

Closure of the handswitch 19 is detected in the electrosurgical generator 14 by monitoring continuity across the pair of contacts 20 and 21 to a reference in the electrosurgical generator 14. If continuity across the pair of contacts 20 and 21 is detected then electrosurgical energy is delivered through conductor 18' from the electrosurgical generator active output connection 34. Another scheme for power control is disclosed in U.S. Pat. 3,752,160 and that is incorporated herein by reference.

While a preferred embodiment and alternatives have been shown in the figures and described in the disclosure, the claims that follow seek to protect replaceable accessory cord set and handswitches for use with electrosurgical instruments.

What is claimed is:

1. In a handswitch set for use with an electrosurgical instrument and an electrosurgical generator, the electrosurgical generator being configured to supply electrosurgical energy and waveforms to the electrosurgical instrument through the handswitch set, wherein the improvement comprises:

a handswitch set including a handswitch and a cord set, the cord set configured for electrically connecting the electrosurgical generator with an electrosurgical instrument, the generator including at least three conjugating connections, the at least three conjugating connections being configured for supplying electrosurgical energy, a cutting waveform, and a coagulating waveform;

a button positioned on the handswitch, the button configured to close a pair of contacts, the pair of contacts including a first contact and a second contact normally in an open position, the closing of the pair of contacts being detectable by the electrosurgical generator such that, upon detection of closure, the electrosurgical generator delivers electrosurgical energy through an active conductor to the first contact; and a switch positioned on the handswitch set for selecting between a cutting waveform and a coagulating waveform, the switch connected with the second contact.

2. The handswitch set of claim 1, wherein the handswitch is adapted to be mounted to the electrosurgical instrument using a pressure sensitive adhesive.

3. The handswitch set of claim 1, wherein the handswitch set includes a support for mounting on the electrosurgical instrument.

4. The handswitch set of claim 3, wherein the support includes the handswitch and the button.

5. The handswitch set of claim 2, wherein the button is configured to actuate the switch for selecting between the two waveforms.

6. The handswitch set of claim 2, wherein the cord set includes a cord, the cord connecting the handswitch to the cord set for the remote positioning of the handswitch from the cord set.

7. The handswitch set of claim 3, wherein the support includes a terminal and the cord set includes a receptacle, the terminal and receptacle configured to electrically connect.

8. The handswitch set of claim 3, wherein the electrosurgical instrument includes a handle having a trigger portion and the support is configured to conformingly mount with the trigger portion, the support also defining a cut-out for the distal end of the electrosurgical instrument.

9. In a handswitch set configured for use with an electrosurgical instrument and an electrosurgical generator, the electrosurgical generator being configured to supply electrosurgical energy and waveforms to the electrosurgical instrument through the handswitch set, the electrosurgical instrument including a distal end with end effectors and a proximal end having a stationary portion and a pivoting portion, wherein the improvement comprises:

a handswitch set including a cord set, the cord set configured for electrically connecting the electrosurgical generator with an electrosurgical instrument, the electrosurgical instrument having a distal end a proximal end, the distal end including at least one end effector and defining a longitudinal axis, the electrosurgical instrument including a handle on the proximal end, the handle including a stationary portion having a trigger portion and a pivoting portion, the stationary portion approximately orthogonal to the axis of the end effectors, and the electrosurgical instrument including at least one end effector on the distal end;

the generator configured for at least supplying electrosurgical energy, a cutting waveform, and a coagulating waveform, the electrosurgical generator configured for the delivery through the active conductor of electrosurgical energy to the first contact;

a support configured to conformingly mate with a stationary portion of the handle, the support defining a recess configured and dimensioned for receiving the distal end of the instrument and the support defining a hole configured for the positioning of a handswitch, the hole defined in the support positioned in juxtaposition with the trigger portion of the handle; and a button positioned in the hole on the handswitch, the button configured to close a pair of contacts normally in an open position, the pair of contacts including a first contact and a second contact, the closing of the contacts by the button resulting in the delivery of electrosurgical energy to the at least one end effector through the first contact and the connecting of one of two waveforms with the first contact, the waveforms including a cutting waveform and a coagulating waveform.

10. The handswitch set of claim 9, wherein the handswitch is adapted to be positioned on the stationary handle and directly connected to the cord set.

11. The handswitch set of claim 9, wherein the support includes a terminal and the terminal is configured to connect with a receptacle of the cord set.

12. The handswitch set of claim 9, wherein the button is adapted to be positioned on a trigger portion of the stationary handle for delivery of electrosurgical energy.

* * * * *